United States Statutory Invention Registration [19]

[11] Reg. Number: H930

Kato et al.

[43] Published: Jun. 4, 1991

[54] DRY-TYPE GLUCOSE ANALYZING ELEMENT

[75] Inventors: Keiko Kato; Fuminori Arai; Harumi Katsuyama, all of Saitama, Japan

[73] Assignee: Fuji Photo Film Co., Ltd., Kanagawa, Japan

[21] Appl. No.: 321,977

[22] Filed: Mar. 10, 1989

[30] Foreign Application Priority Data

Mar. 11, 1988 [JP] Japan ..... 63-57786

[51] Int. Cl.[5] ..... C12Q 1/54; C12Q 1/26; C12Q 1/28

[52] U.S. Cl. ..... 435/14; 435/25; 435/28; 435/805

*Primary Examiner*—John S. Maples
*Assistant Examiner*—Philip Tucker
*Attorney, Agent, or Firm*—Jules E. Goldberg

[57] ABSTRACT

A dry-type quantitative glucose-analyzing element comprising a water-impermeable light-transmissive support having thereon a group of water-permeable layers comprising a reagent layer, an enzyme-containing layer, and a porous spreading layer which are laminated on said support in this order, and a hydrogen peroxide-detecting coloring composition comprising a hydrogen donor and a coupler; wherein said reagent layer contains at least said coupler;

said enzyme-containing layer contains a glucose oxidase, a peroxidase and a mordant which immobilizes a dye formed by said coloring composition; and said hydrogen donor is contained in at least one water-permeable layer of said group. Using the element, quantitative determination of glucose of high concentration is possible with high accuracy.

11 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DRY-TYPE GLUCOSE ANALYZING ELEMENT

FIELD OF THE INVENTION

The present invention relates to a dry-type quantitative glucose-analyzing element.

BACKGROUND OF THE INVENTION

JP-A-60-82859 (the term "JP-A" as used herein means an "unexamined published Japanese patent application"; corresponding patent written in English or German are shown after the Examples hereof) illustrates a quantitative glucose analyzing element having an oxidase layer. This dry-type quantitative glucose-analyzing element is characterized in that it contains a peroxidase in the reagent layer. However, it has a drawback in that the accuracy of quantitative analysis of glucose is lower in the higher concentration range due to the smaller gradient of the calibration curve in the higher concentration range.

SUMMARY OF THE INVENTION

An object of the present invention is to provide a dry-type glucose-analyzing element, in which the calibration curve possesses a sufficient gradient, even in the high concentration range, such that quantitative analysis of glucose with high accuracy is possible up to the high concentration range.

The object can be attained by a dry-type quantitative glucose-analyzing element comprising a water-impermeable light-transmissive support having thereon a group of water-permeable layers comprising a reagent layer, an enzyme-containing layer, and a porous spreading layer which are laminated on said support in this order, and a hydrogen peroxide-detecting coloring composition comprising a hydrogen donor and a coupler; wherein said reagent layer contains at least said coupler;

said enzyme-containing layer contains a glucose oxidase, a peroxidase and a mordant which immobilizes dye formed by said coloring composition; and said hydrogen donor is contained in out least one water-permeable layer of said group.

DETAILED EXPLANATION OF THE INVENTION

Figure 1:
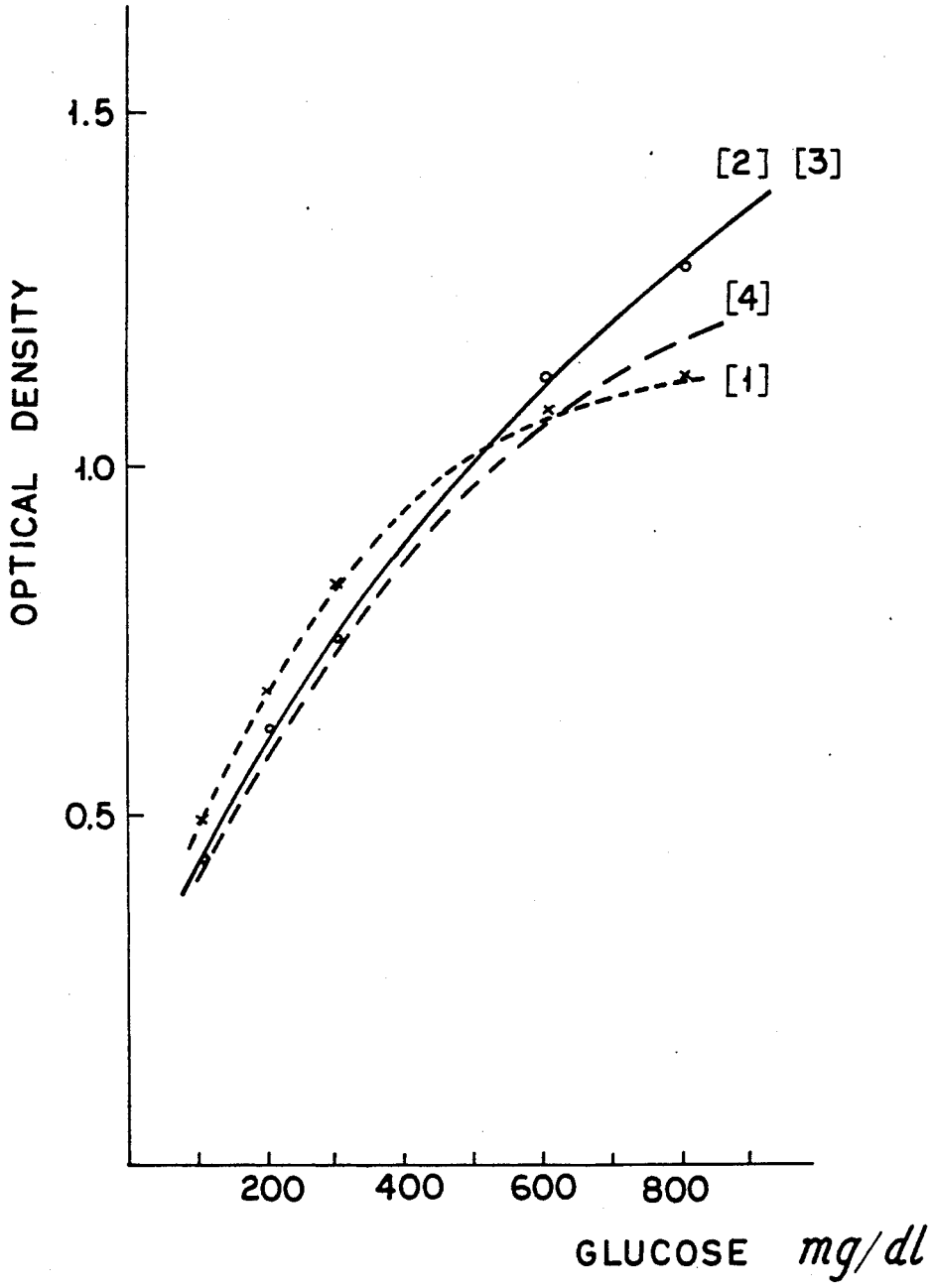
FIG. 1 is a graph showing the variation of optical density versus glucose concentration obtained in Example of Analysis.

The hydrogen donor is, for example, 4-aminoantipyrine or 4-amino-2-methyl-3-phenyl-1-(2,4,6-trichlorophenyl)-3-pyrazolin-5-one.

The hydrogen donor may be incorporated in at least one of the water permeable layers, such as, the reagent layer and the enzyme-containing layer. The amount of the hydrogen donor in the element is generally from 0.2 to 5 g/m$^2$.

Examples of the coupler contained in the reagent layer include 1,7-dihydroxynaphthalene, phenol and $\alpha$-naphthol. The amount of the coupler in the reagent layer is generally from 0.1 to 3 g/m$^2$.

The reagent layer of the analysis element of the present invention is preferably a non-porous substantially uniform layer having a hydrophilic polymer, such as gelatin, gelatin derivatives, e.g., phthalated gelatin, polyacrylamide or polyvinyl pyrrolidone, as a binder.

The reagent layer may also be a porous layer. Suitable for use as the reagent layer are a fibrous porous layer, such as, filter paper and non-woven fabric, and a non-fibrous porous layer, such as, a blush polymer layer made of cellulose esters, for example, cellulose acetate or cellulose acetate/butyrate, as described in U.S. Pat. Nos. 1,421,341 and 3,992,158; a fine porous layer made of polysulfone, as described in JP-A-62-27006; a porous layer comprising polymer beads, glass beads or diatomaceous earth grains bonded with a hydrophilic or non-hygroscopic polymer and having continuous voids therein, as described in U.S. Pat. No. 3,992,158 and JP-A-55-90859; and a polymer grain structural article as described in JP-A-57-101760 and 57-101761.

The thickness of the reagent layer is generally from 2 to 30 $\mu$m.

As the mordant used in the enzyme-containing layer, cationic polymers, for example, tertiary amino group-containing polymers or quaternary ammonium group-containing polymers, are preferred. The molecular weight of the polymer is generally from 5,000 to 200,000.

Examples of such polymers include polymers having vinylpyridinium cations as described in U.S. Pat. Nos. 2,548,564, 2,484,430, 3,148,061 and 3,756,814 and JP-A-52-136626; polymers crosslinkable with gelatin described in U.S. Pat. Nos. 3,625,694, 3,859,096 and 4,128,538 and British Patent No. 1,277,453; aqueous sol-type cationic polymers described in U.S. Pat. Nos. 3,958,995, 2,721,852 and 2,798,063, JP-A-54-115228, 54-145529 and 54-126027; water-insoluble cationic polymers described in U.S. Pat. No. 3,898,088 and JP-A-55-33172; reactive mordants capable of forming covalent bond with dyes, described in U.S. Pat. No. 4,168,976 (corresponding to JP-A-137333); and cationic polymers described in U.S. Pat. Nos. 3,709,690, 3,788,855, 3,642,482, 3,488,706, 3,557,066, 3,271,147 and 3,271,148, JP-A-50-71332, 53-30328, 52-155528, 53-125 and 53-1024.

In addition, there are cationic polymers described in U.S. Pat. Nos. 2,675,316 and 2,882,156.

Preferred among those are polymers which exhibit minimal mobility from an enzyme-containing layer, which preferably comprises a hydrophilic colloid, to other layers. For instance, substances capable of being crosslinked with a hydrophilic colloid, such as, gelatin, as well as water-insoluble cationic polymers and aqueous sols of a solid or a liquid or latex dispersions are preferably used.

Particularly preferred cationic polymers are mentioned below.

(1) Polymers having quaternary ammonium groups and groups capable of bonding with gelatin by a covalent bond, for example, aldehyde group, chloroalkanoyl group, chloroalkyl group, vinylsulfonyl group, pyridiniumpropionyl group, vinylcarbonyl group or alkylsulfonoxy group, such as:

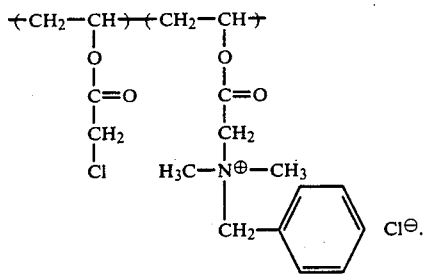

(2) Reaction products of copolymers composed of repeating units of monomers of the following general formula (VII) and repeating units of other ethylenic unsaturated monomers, and crosslinking agents, for example, bisalkanesulfonates or bisallenesulfonates.

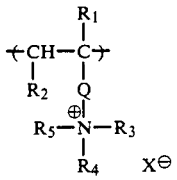

(VII)

wherein $R_1$ represents a hydrogen atom or an alkyl group, preferably having 1 to 2 carbon atoms; $R_2$ represents a hydrogen atom, an alkyl group, preferably having 1 to 2 carbon atoms, or an aryl group, preferably having 6 to 10 carbon atoms;

Q represents a divalent group, e.g., ethylene, phenylene and $-C_6H_4CH_2-$;

$R_3$, $R_4$ and $R_5$ each represents an alkyl group, preferably having 1 to 12 carbon atoms, or an aryl group, preferably having 6 to 10 carbon atoms, or at least two of $R_3$ to $R_5$ may be bonded together to form a heterocyclic ring containing a N atom or further containing at least one of N, O, S and Se atoms.

Examples of heterocyclic rings include pyridine, piperazine, piperidine, morpholine, pyrroline, oxazole, thiazole, and imidazole; $X^{\ominus}$ represent an anion, e.g., $Cl^{\ominus}$, $Br^{\ominus}$, and the above-described alkyl group and aryl group may be substituted with, for example, an aryl group, e.g., phenyl, or an alkyl group, preferably having 1 to 4 carbon atoms, e.g., methyl.

An example of a repeating unit of the polymer represented by formula (VII) is

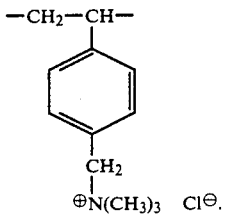

(3) Polymers represented by the following general formula (VIII):

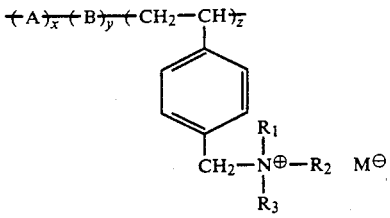

(VIII)

wherein x represents from about 0.25 to about 5 mol %;

y represents from about 0 to about 90 mol %;

z represents from about 10 to about 99 mol %;

A represents a repeating unit derived from a monomer having at least two ethylenic unsaturated bonds, e.g., butadiene;

B represents a repeating unit derived from a copolymerizable ethylenic unsaturated monomer, e.g., vinylene, styrene;

$R_1$, $R_2$ and $R_3$ each represents an alkyl group, preferably having 1 to 12 carbon atoms, or a cyclic hydrocarbon group, or at least two of $R_1$ to $R_3$ may be bonded together to form a ring; and the groups and rings may be substituted with, for example, an alkyl group, preferably having 1 to 4 carbon atoms, e.g., a methyl, and aryl group preferably having 6 to 10 carbon atoms, e.g., phenyl; and $M^{\ominus}$ represents an anion, e.g., $Cl^{\ominus}$, $Br^{\ominus}$.

An example of the polymer represented by formula (VIII) is

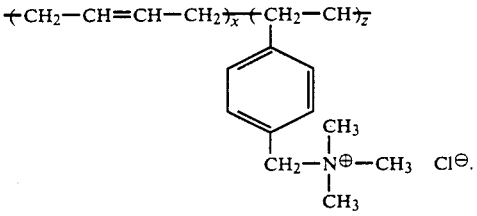

(4) Water-insoluble polymers having a repeating unit represented by the following general formula (IX) in a proportion of ⅓ or more in a molecule.

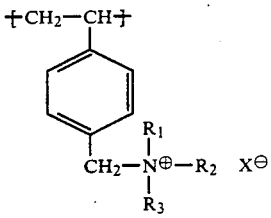

(IX)

wherein $R_1$, $R_2$ and $R_3$ each represents an alkyl group which may be substituted with, for example, a phenyl group, and the total number of the carbon atoms of $R_1$ to $R_3$ is 12 or more; and $X^{\ominus}$ represents an anion (e.g., $Cl^{\ominus}$, $Br^{\ominus}$).

An example of a repeating unit represented by formula (IX) is

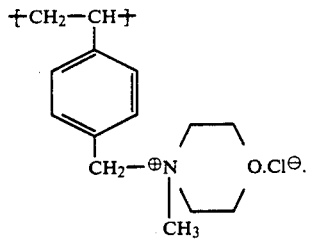

The spreading layer is preferably such that it may supply the sample solution applied thereto to the adjacent water-permeable layer in a substantially even amount per unit area of the layer. The spreading layer is preferably made of a fibrous material, for example wove: clothes as described in JP-A-55-164356 (U.S. Pat. No. 4,292,272) or knitted fabrics as described in European Patent No. 162,302A. Knitted fabrics and other fibrous materials may be subjected to glow discharge treatment, as described in British Patent No. 2,087,074.

A non-fibrous porous layer may also be used as described in U.S. Pat. No. 3,992,158, a porous layer comprising polymer beads, glass beads or diatomaceous earth bonded with hydrophilic or non-water-absorbing polymer and having continuous voids therein as described in U.S. Pat. Nos. 3,992,158 and 4,258,001, and a polymer grain structural article as described in JP-A-57-101760 and 57-101761 can also be used.

The spreading layer can contain a hydrophilic polymer or surfactant as described in European Patent No. 161,301A and West German Patent No. 3,717,913, so as to adjust the spreading area and the spreading rate.

The enzyme-containing layer contains glucose oxidase, peroxidase and a mordant preferably in an amount of from 5,000 to 70,000 units/$m^2$, 10,000 to 150,000 units/$m^2$, and 0.3 to 6 g/$m^2$, respectively.

The enzyme-containing layer may contain a hydrophilic water-permeable polymer as a binder. The binder is preferably 40% to 95% by weight based on the total weight of the enzyme-containing layer. The polymer used in this layer may be selected from the examples disclosed as those for the polymer used in the reagent layer.

The thickness of the enzyme-containing layer is generally from 2 to 30 μm.

The analysis element of the present invention preferably has a light-shielding layer between the spreading layer and the enzyme-containing layer. The light-shielding layer acts to shield the color of the sample solution as it is applied dropwise to the spreading layer. This is especially important for the red color of hemoglobin when the sample is whole blood, or the yellow color of bilirubin, in the determination of the detectable change, i.e., color change, coloration, as created in the reagent layer by the measurement of reflected light, or, as the case may be, partly in the enzyme-containing layer, from the side of the light-transmissive support. It also acts as a light-reflection layer or background layer.

In the present invention, the light-shielding layer is preferably oxygen-permeable and more preferably it is also protein-impermeable. "Oxygen-permeable" and "protein-impermeable" means that oxygen ($O_2$) in air is substantially permeable through the layer, and that proteins are substantially impermeable therethrough, respectively, under analysis conditions, i.e., when water, as a solvent in an aqueous liquid sample or a blood sample penetrates into the layer, so that the layer is thereby wetted or swollen. The "proteins" as herein referred to are proteins within the ordinary meaning of the word having a molecular weight of about 5,000 or more, which specifically include hemproteins, such as, hemoglobin (having a molecular weight of about 65,000) as well as conjugated proteins having a hydrogen peroxide-decomposing activity, such as, catalase (having a molecular weight of about 250,000).

The oxygen-permeable protein-impermeable light-shielding layer is a substantially non-porous layer which contains light-shielding and light-reflective fine particles, e.g., titanium dioxide particles in the form of a dispersion in a small amount of hydrophilic (or weakly hydrophilic) polymer binder.

Examples of such light-shielding fine particles include titanium dioxide fine particles, barium sulfate fine particles, carbon black, etc. Among these, titanium dioxide fine particles and barium sulfate fine particles are preferred.

The titanium dioxide fine particles which can be contained in the light-shielding layer are titanium dioxide fine particles which are not surface treated, i.e., generally surface-coated, with an aluminium compound composed of a trivalent aluminium and oxygen, such as, aluminium oxide (alumina, $Al_2O_3$) or hydrated oxide of aluminium (e.g., alumina hydrate, $Al_2O_3.H_2O$, $Al_2O_3.3H_2O$), or a substance composed of a trivalent aluminum, other elements, e.g., tetravalent silicon, and oxygen, or titanium dioxide fine particle which are not surface treated with silicon oxide. (These particles will be referred to hereunder as a "non-surface-treated titanium dioxide fine particles".) The titanium dioxide fine particles may have any crystalline form of the anatase type, rutile type or brookite type. The mean grain size of the fine particles may be from about 0.1 μm to about 1.0 μm, and preferably from about 0.15 μm to about 0.5 μm, for commercially available products. Specific examples of titanium dioxide fine particles suitable for use in the present invention are non-surface-treated titanium dioxide fine particles and titanium dioxide fine particles surface-treated with titanium hydroxide. Among these, the former non-surface-treated titanium dioxide fine particles are preferred.

As examples of hydrophilic (or weakly hydrophilic) polymer binders, there are gelatins (e.g., arid-processed gelatin, de-ionized gelatin), gelatin derivatives (e.g., phthalated gelatin, hydroxymethyl acrylate-grafted gelatin), polyvinyl alcohol, regenerated cellulose and cellulose acetates (e.g., cellulose diacetate). them, preferred are gelatins and gelatin derivatives. Gelatins and gelatin derivatives can be used together with conventional hardening agents (crosslinking agents).

The ratio of the fine particles and the polymer binder in the light-shielding layer in a dry state may be such that the light-shielding layer is non-porous to such an extent that the oxygen-permeability and, at the same time, the protein-impermeability are maintained. The non-porous layer may have such fine pores that the mean pore size is smaller than that capable of expressing the spreading function or metering function in the porous spreading layer but have substantially neither a spreading nor metering function. Specifically, the ratio of the fine particles to the polymer binder (dr) basis) is generally within the range of about 10:2.5 to 10:7.5, preferably about 10:3.0 to 10:6.5, by volume. When the fine particles are titanium dioxide particles, the ratio of the titanium dioxide to the polymer binder (dry basis) is generally within the range of about 10:0.6 to 10:1.8, and preferably about 10:0.6 to 10:1.5 by weight. The dry thickness of the light-shielding layer is from 3 to 30 μm, and preferably from about 5 μm to about 20 μm.

An interlayer may optionally be provided between the reagent layer and the enzyme-containing layer, or between the enzyme-containing layer and the light-shielding layer, if desired. As the interlayer, a film-forming hydrophilic polymer similar to that used in the reagent layer may be used. The thickness of the interlayer is generally from about 0.2 μm to about 10 μm, and preferably from about 0.5 μm to about 7 μm An adhesive layer for adhering and laminating the spreading layer may be provided on the enzyme-containing layer or light-shielding layer. The adhesive layer is generally made of a hydrophilic polymer, such as gelatin, gelatin derivatives, polyacrylamide or starch, which may adhere to the porous layer when swollen with water.

The reagent layer, enzyme-containing layer and adhesive layer can contain activating agents for enzymes and coenzymes, buffers, film hardening agents and surfactants, if desired. As buffers, there may be mentioned carbonates, borates, phosphates as well as Good's buffers described in Biochemistry, Vol. 5, No. 2, pages 467 to 477 (1966).

The following examples are intended to illustrate the present invention but not to limit it in any way.

EXAMPLE 1

(1) Support, Reagent Layer

An aqueous solution having the composition shown below was coated on a colorless transparent polyethylene terephthalate (PET) flat film of 180 μm in thickness, with a gelatin subbing layer by a conventional method and dried to form a film thereon having a dry thickness of about 15 μm.

| Coating Composition for the Reagent Layer: | |
|---|---|
| Gelatin | 33 g |
| 1,7-Dihydroxynaphthalene | 1.03 g |
| Polyoxyethylene Nonylphenyl Ether | 0.33 g |
| Water | 200 ml |

(2) Enzyme-containing Layer

An aqueous solution having the composition shown below was superimposed over the reagent layer and dried to form a film having a dry thickness of about 3 pm (enzyme-containing layer).

| | |
|---|---|
| Gelatin | 15 g |
| Peroxidase | 0.52 g |
| Glucose oxidase | 0.22 g |
| Styrene/P{(1-methyl-1-piperazino)methyl} styrene/Divinylbenzene Copolymer | 7.5 g |
| Divinylsulfone | 0.40 g |
| Polyoxyethylene Nonylphenyl Ether | 0.33 g |
| 4-Amino-2-methyl-3-phenyl-1-(2,4,6-trichlorophenyl)-3-pyrazolin-5-one | 5.2 g |
| Water | 200 ml |

(3) Light Shielding Layer

A liquid composition shown below was coated over the enzyme-containing layer and dried, to form an oxygen-permeable protein-impermeable light-shielding layer having a dry thickness of about 7 μm.

| Coating Composition for the Light-shielding Layer: | |
|---|---|
| Titanium Dioxide (average size 0.2 μm) | 100 g |
| Gelatin | 10 g |
| Polyoxyethylene p-Nonylphenyl Ether | 0.33 g |
| Water | 200 ml |

(4) Adhesion Layer

A liquid composition shown below was coated over the light-shielding layer and dried, to form an adhesion layer having a dry thickness of about 2 μm.

| Coating Composition for the Adhesion Layer: | |
|---|---|
| Gelatin | 9.8 g |
| Polyoxyethylene Nonylphenyl Ether | 0.33 g |
| Water | 200 ml |

(5) Spreading Layer

Thereafter, distilled water was applied to the surface of the adhesive layer in a proportion of about 30 g/m$^2$ so as to moisten the sample, and then a tricot-knitted fabric made of polyester yarns was tightly attached thereto and dried by passing it through laminating rolls. An integrated multi-layer analyzing element (1) for quantitative determination of glucose was thus prepared.

EXAMPLE 2

A quantitative glucose-analyzing element (2) was prepared in the same manner as in Example 1, except that 4-amino-2-methyl-3-phenyl-1-(2,4,6-trichlorophenyl)-3-pyrazolin-5-one in the enzyme-containing layer composition in Example 1 was replaced by 4-aminoantipyrine (3.4 g).

EXAMPLE 3

A quantitative glucose-analyzing element (3) was prepared in the same manner as in Example 2, except that 4-aminoantipyrine in the enzyme-containing layer composition in Example 2 was omitted and instead 4-aminoantipyrine (2.0 g) was added to the coating composition for the reagent layer.

COMPARATIVE EXAMPLE 1

A comparative analyzing element was prepared as mentioned below, in accordance with the technique of preparing a glucose-analyzing element containing an oxidase layer described in JP-A-60-82859.

Peroxidase was omitted from the enzyme-containing layer composition in Example 1, and instead peroxidase (0.23 g) was added to the coating composition for the reagent layer. The other layers were same as those in Example 1, and a comparative glucose-analyzing element (4) was prepared.

EXAMPLE OF ANALYSIS

Glucose was added to a human whole blood sample to obtain various samples having different glucose concentrations of up to 1000 mg/dl. Calibration curves were made for the analyzing elements (1) to (4), using the thus prepared blood samples respectively, from the data measured and shown in Table 1 below (the numerals indicate the spectral reflection density). The calibration curves are shown in the graph of FIG. 1. The analyzing elements (1) to (3) of the present invention maintained a measurable gradient of the calibration curves up to the high glucose concentration, indicating a noticeable improvement in the quantitative accuracy at high glucose concentrations over the comparative analyzing element (4).

TABLE 1

| Analyzing Element | Concentration of Glucose (mg/dl) | | | | |
|---|---|---|---|---|---|
| | 100 | 200 | 300 | 600 | 800 |
| (1) | 0.442 | 0.607 | 0.746 | 1.063 | 1.178 |
| (2) | 0.435 | 0.622 | 0.753 | 1.125 | 1.281 |
| (3) | 0.433 | 0.620 | 0.748 | 1.122 | 1.277 |
| (4) | 0.493 | 0.681 | 0.829 | 1.075 | 1.115 |

U.S. Patents or West German Patents corresponding to the Japanese publications cited in this application are as follows.

| | |
|---|---|
| JP-A-60-82859 | EP 137,521A |
| JP-A-54-115228 | DE 2,905,652 |
| JP-A-55-33172 | U.S. Pat. No. 4,312,940 |
| JP-A-50-71332 | U.S. Pat. No. 4,124,386 |
| JP-A-53-30328 | U.S. Pat. No. 4,131,469 |
| JP-A-53-125 | U.S. Pat. No. 4,154,615 |
| JP-A-53-1024 | U.S. Pat. No. 4,142,899 |

While the invention has been described in detail and with reference to specific embodiments thereof, it will be apparent to one skilled in the art that various changes and modifications can be made therein without departing from the spirit and scope thereof.

What is claimed is:

1. A dry-type quantitative glucose-analyzing element comprising a water-impermeable light-transmissive support having thereon a group of water-permeable layers comprising a reagent layer, an enzyme-containing layer, and a porous spreading layer which are laminated on said support in this order, and a hydrogen peroxide-detecting coloring composition comprising a hydrogen donor and a coupler; wherein said reagent layer contains at least said coupler;

said enzyme-containing layer contains a glucose oxidase, a peroxidase and a mordant which immobilizes a dye formed by said coloring composition; and said hydrogen donor is contained in at least one water-permeable layer of said group.

2. A dry quantitative glucose-analyzing element as in claim 1, wherein said group further comprises a light-shielding layer between the enzyme-containing layer and the spreading layer.

3. A dry quantitative glucose-analyzing element as in claim 2, wherein said light-shielding layer is oxygen-permeable and protein-impermeable.

4. A dry quantitative glucose-analyzing element as in claim 1, wherein said hydrogen donor is contained in at least one of the reagent layer and the enzyme-containing layer.

5. A dry quantitative glucose-analyzing element as in claim 4, wherein said hydrogen donor is contained in the enzyme-containing layer.

6. A dry quantitative glucose-analyzing element as in claim 4, wherein said hydrogen donor is contained in the reagent layer.

7. A dry quantitative glucose-analyzing element as in claim 2, wherein said hydrogen donor is contained in at least one of the reagent layer and the enzyme-containing layer.

8. A dry quantitative glucose-analyzing element as in claim 1, wherein said enzyme containing layer contains glucose oxidase in an amount of from 5,000 to 70,000 units/$m^2$.

9. A dry quantitative glucose-analyzing element as in claim 1, wherein said enzyme containing layer contains peroxidase in an amount of from 10,000 to 150,000 units/$m^2$.

10. A dry quantitative glucose-analyzing element as in claim 1, wherein said enzyme containing layer contains said mordant in an amount of from 0.3 to 6 g/$m^2$.

11. A dry quantitative glucose-analyzing element as in claim 1, wherein said enzyme containing layer has a thickness of from 2 to 30 $\mu$m.

* * * * *